US008148676B2

(12) United States Patent
LeMaire et al.

(10) Patent No.: US 8,148,676 B2
(45) Date of Patent: Apr. 3, 2012

(54) USE OF IONIC MATRICES FOR MALDI MASS SPECTROMETRY ANALYSIS OF TISSUE SECTIONS

(75) Inventors: Rémi LeMaire, Sucy en Brie (FR); Isabelle Fournier, Bourghelles (FR); Michel Salzet, Bourghelles (FR); Jean-Claude Edmond Tabet, Morangis (FR)

(73) Assignees: Centre National de la Recherche Scientifique (CNRS), Paris (FR); Universite des Sciences et Technologies de Lille, Villeneuve d'Asq (FR)

( * ) Notice: Subject to any disclaimer, the term of this patent is extended or adjusted under 35 U.S.C. 154(b) by 2 days.

(21) Appl. No.: 11/916,558

(22) PCT Filed: Jun. 7, 2006

(86) PCT No.: PCT/IB2006/002311
§ 371 (c)(1),
(2), (4) Date: Dec. 5, 2007

(87) PCT Pub. No.: WO2007/007192
PCT Pub. Date: Jan. 18, 2007

(65) Prior Publication Data
US 2008/0203289 A1 Aug. 28, 2008

Related U.S. Application Data

(60) Provisional application No. 60/687,848, filed on Jun. 7, 2005.

(51) Int. Cl.
*B01D 59/44* (2006.01)

(52) U.S. Cl. ......... 250/282; 436/173; 250/281; 250/288
(58) Field of Classification Search .................. 250/282, 250/288; 436/173
See application file for complete search history.

(56) References Cited

U.S. PATENT DOCUMENTS

| 5,808,300 | A | * | 9/1998 | Caprioli ........................ 250/288 |
| 6,635,452 | B1 | | 10/2003 | Monforte et al. |
| 6,824,981 | B2 | | 11/2004 | Chait et al. |
| 2002/0171037 | A1 | * | 11/2002 | Ellson et al. ................... 250/288 |
| 2005/0158863 | A1 | * | 7/2005 | Stahl et al. ........................ 436/8 |
| 2006/0121535 | A1 | | 6/2006 | Brueggemeier et al. |
| 2006/0198820 | A1 | | 9/2006 | McDonald et al. |

FOREIGN PATENT DOCUMENTS

| DE | 102 38 069 A1 | 3/2004 |
| WO | WO 95/04160 A1 | 2/1995 |
| WO | WO 97/27327 A2 | 7/1997 |
| WO | WO 98/26095 A1 | 6/1998 |
| WO | WO 00/68434 A2 | 11/2000 |
| WO | WO 2004/051270 A2 | 6/2004 |

(Continued)

OTHER PUBLICATIONS

International Search Report mailed on Dec. 1, 2006 for application No. PCT/IB2006/002311.

(Continued)

*Primary Examiner* — Michael Maskell
(74) *Attorney, Agent, or Firm* — Foley & Lardner LLP

(57) ABSTRACT

The invention concerns improved methods for studying peptides/proteins expression in a tissue section or for determining at least one compound, in particular a protein, expression map in a tissue section, using ionic MALDI matrices.

11 Claims, 11 Drawing Sheets

FOREIGN PATENT DOCUMENTS

| WO | WO 2005/067648 A2 | 7/2005 |
|---|---|---|
| WO | WO 2005/113804 | 12/2005 |

OTHER PUBLICATIONS

Armstrong et al., *Anal. Chem.*, 2001, 73(15): pp. 3679-3686.
Sze et al., *J. Am. Soc. For Mass Spectrometry*, Feb. 1998, 9(2): pp. 166-174.
Mank et al., *Anal. Chem.*, 2004, 76(10), pp. 2938-2950.
LeMaire et al., *Anal. Chem.*, 2006, 78(3): pp. 809-819.
Caprioli et al., *Anal. Chem.*, 1997, 69(23): pp. 4751-4760.
Carda-Broch et al., *Rapid Commun. Mass Spectrom.*, 2003, 17: pp. 553-560.
Chaurand et al., *Anal. Chem.*, Mar. 1, 2004, pp. 87A-93A.
Chaurand et al., *Proc. 52$^{nd}$ ASMS Conf. on Mass Spectrom. and Allied Topics*, May 23-27, 2004, Nashville, Tennessee.
Karas et al., *Anal. Chem.*, 1988, 60: pp. 2299-2301.
Li et al., *J. Am. Soc. for Mass Spectrom.*, 2004, 15: pp. 1833-1837.
Zabet-Moghaddam et al., *Rapid Commun. Mass Spectrom.*, 2004, 18: pp. 141-148.
International Search Report issued on Oct. 8, 2007 in application No. PCT/IB2006/02309.
Caprioli et al., "Molecular Imaging of Biological Samples: Localization of Peptides and Proteins Using MALDI-TOG MS," *Anal. Chem.*, 1997, vol. 69, pp. 4751-4760.
U.S. Appl. No. 11/921,678, filed Jun. 7, 2006, LeMaire et al.
Cooks et al., "Ambient Mass Spectrometry," *Science*, Mar. 17, 2006, vol. 311, pp. 1566-1570.
Toubol et al., "Improvement of Biological Time-of-Flight-Secondary Ion Mass Spectrometry Imaging with a Bismuth Cluster Ion Source," *J. Am. Soc. Mass. Spectrom.*, 2005, vol. 16, pp. 1608-1618.
Bai et al., "Design and synthesis of a photocleavable biotinylated nucleotide for DNA analysis by mass spectrometry," *Nucleic Acids Research*, 2004, vol. 32, No. 2, pp. 535-541.
Bai et al., "Photocleavage of a 2-nitrobenzyl linker bridging a fluorophore to the 5' end of DNA," *PNAS*, Jan. 21, 2003, vol. 100, No. 2, pp. 409-413.
Olejnik et al., "Photocleavable peptide-DNA conjugates: synthesis and applications to DNA analysis using MALDI-MS," *Nucleic Acids Research*, 1999, vol. 27, No. 23, pp. 4626-4631.
Levi-Setti et al., "Imaging of BrdU-Labeled Human Metaphase Chromosomes with a High Resolution Scanning Ion Microprobe," *Microscopy Research and Technique*, 1997, vol. 36, pp. 301-312.
Stoeckli et al., "Imaging mass spectrometry: A new technology for the analysis of protein expression in mammalian tissues," *Nature Medicine*, Apr. 2001, vol. 7, No. 4, pp. 493-496.
Walter, "Molecular Targeted Radiation Therapy," *S&TR*, Jul./Aug. 2003, pp. 10-11.
Wenzel et al., "Genosnip: SNP Genotyping by MALDI-TOF MS Using Photocleavable Oligonucleotides," *Nucleosides, Nucleotides & Nucleic Acids*, 2003, vol. 22, Nos. 5-8, pp. 1579-1581.
Wisztorski, et al. "New Developments in MALDI Imaging for Pathology Proteomic Studies" *Current Pharmaceutical Design*, 2007, vol. 13, pp. 3317-3324.
Franck, et al. "Improving Tissue Preparation for Matrix-Assisted Laser Desorption Ionization Mass Spectrometry Imaging. Part 1: Using Microspotting" *Analytical Chemistry*, 2009, pp. A-J.
Moench, "In situ huybridization," *Molecular and Cellular Probes*, vol. 1, pp. 195-205, 1987.
Stoeckli et al., "Automated Mass Spectrometry Imaging with a Matrix-Assisted Laser Sesorption Ionization Time-of-Flight Instrument," *J. Am. Soc. Mass Spectrom.*, vol. 10, pp. 67-71, 1999.

* cited by examiner

A

B

Positive polarity m/z 1212 + m/z 1670   m/z 1758 + m/z 1869   m/z 2468   m/z 4971

Negative polarity m/z 1529 + m/z 1582   m/z 1269 + m/z 2007   m/z 1268   m/z 2007

USE OF IONIC MATRICES FOR MALDI MASS SPECTROMETRY ANALYSIS OF TISSUE SECTIONS

The invention concerns improved methods for studying peptides/proteins expression in a tissue section or for determining at least one compound, notably peptides/proteins, expression map in a tissue section, using ionic MALDI matrices.

Recently, transcriptome and proteome studies have led to the identification of many proteins implicated in a wide diversity of diseases, such as several kinds of cancers.

However, most of these results have been obtained on purified extracted nucleic acid or protein samples, which do not generate information on the tissue localisation of the incriminated proteins, although this kind of information is crucial for the understanding of physiological processes.

Mass spectrometry allows for the simultaneous multiplex analysis of complex mixtures of biomolecules, depending on their molecular weight. In particular, Matrix Assisted Laser Desorption/Ionization (MALDI) mass spectrometry has become a powerful tool in the field of biological researches and is used for the detection, identification and characterization of nucleic acids, peptides and proteins from complex mixtures.

In addition, several publications have shown that MALDI-MS could become an efficient tool for direct analysis of peptides and proteins in tissue sections (Caprioli, R. M.; Farmer, T. B.; Gile, J. Anal. Chem. 1997, 69, 4751-4760; Stoeckli, M.; Farmer, T. B.; Caprioli, R. M. Nat. Med. 2001, 7, 493-496; Chaurand, P.; Schwartz, S. A.; Caprioli, R. M. Anal. Chem. 2004, 87A-93A).

However, many difficulties still impede the routine use of such a technology for the global analysis of peptides and proteins in tissue sections. Indeed, direct tissue analysis generally leads in some extend to a lowered spectral quality due to the tissue e.g. the thickness, the freezing date, nature of the tissue (Caprioli, R. M.; Farmer, T. B.; Gile, J. Anal. Chem. 1997, 69, 4751-4760; Stoeckli, M.; Farmer, T. B.; Caprioli, R. M. Nat. Med. 2001, 7, 493-496; Chaurand, P.; Schwartz, S. A.; Caprioli, R. M. Anal. Chem. 2004, 87A-93A). Significant ameliorations of the current technologies are needed for this technology to become a really powerful tool, notably in term of resolution, sensitivity, increase of the analysis duration, and possibility to use several different modes of analysis, especially the Post Source Decay (PSD) or MS/MS analysis modes which allow to get structural information Along this line, different teams try to find the possibility to enhance signal intensity, detection and/or resolution using cryodetector (Chaurand, P.; Hayn, G.; Matter, U.; Caprioli, R. M.; Poster presented at the 52$^{nd}$ ASMS conference, Nashville, USA, 2004) for MALDI in case of proteins larger than 100 kDa or using MALDI Tof-Tof.

Another alternative can be chosen by developing new matrices for MALDI. In fact, matrix play an essential role on desorption/ionization mechanisms in MALDI. Thus, spectral quality i.e. peak resolution, sensitivity, intensity and Signal/Noise ratio, is dependant to the choice of the matrix. Current commonly used matrices for peptide/protein analysis, such as α-cyano-4-hydroxycinnamic acid (CHCA), 2,5-dihydroxybenzoic acid (2,5-DHB) and sinapinic acid (SA), cannot prevent a lowered spectral quality in the direct analysis of tissue sections. Hence it is necessary to develop new matrices for direct peptide/protein analysis in tissue sections.

The properties of a new better matrix for MALDI Imaging compared to commonly used CHCA, SA, and 2,5DHB matrices should be:

1) a better spectral quality in term of resolution, sensitivity, intensity, Signal/Noise ratio, number of compounds detected, contaminants tolerance, 2) a better crystallization on tissues i.e. covering capacity, homogeneity of crystallization, homogeneity of crystal sizes and time of crystallization, and 3) a better analysis duration in term of vacuum stability.

4) smaller volumes of materials ejected during desorption process

Recently, ionic matrices, prepared by an acid-base reaction between an acid conventional MALDI matrix and an organic base, have been generated (Armstrong, D. W.; Zhang, L. K.; He, L.; Gross, M. L. Anal. Chem. 2001, 73, 3679-3686; Carda-Broch, S.; Berthold, A.; Armstrong, D. W. Rapid Commun. Mass Spectrom. 2003, 17, 553-560). Tested on standards, they showed high stability under vacuum conditions and improved signal intensity and reproducibility compared to conventional matrices (Armstrong, D. W.; Zhang, L. K.; He, L.; Gross, M. L. Anal. Chem. 2001, 73, 3679-3686; Carda-Broch, S.; Berthold, A.; Armstrong, D. W. Rapid Commun. Mass Spectrom. 2003, 17, 553-560; Mank, M.; Stahl, B.; Boehm, G. Anal. Chem. 2004, 63, 3679-3686; Moghaddam, M. Z.; Heinzle, E.; Tholey, A. Rapid Commun. Mass Spectrom. 2004, 18, 141-148).

Surprisingly, since the performances of conventional matrices are significantly decreased in direct tissue section analysis, the inventors found that ionic matrices keep their improved performances in direct tissue section analysis, greatly improving the spectral quality both in term of resolution, sensitivity, intensity, Signal/Noise ratio, number of compounds detected, and contaminants tolerance. Moreover, ionic matrices allow for a better analysis duration in term of vacuum stability, can be used in both positive and negative modes and give the possibility to perform Post Source Data (PSD) or MS/MS analyses on cuts to get structural information. Finally, at least some of the tested ionic matrices gave a better crystallization on tissues in term of covering capacity, homogeneity of crystallization, homogeneity of crystal sizes and time of crystallization.

The inventors have thus developed tools that improve the reproducibility, the sensitivity, and the precision of the detection of compounds, in particular proteins, in tissue sections using mass spectrometry, in particular MALDI mass spectrometry.

The invention thus concerns a method for studying protein expression in a tissue section, comprising:

1) applying a ionic MALDI matrix onto the tissue section, 2) scanning the tissue section with a MALDI mass spectrometer and saving the resulting data, and 3) in each analyzed point, determining the protein composition by comparing the obtained spectrum with database proteins molecular weights and spectra.

Several useful protein database are available on the internet (see following Table 1) that provide various information on proteins, including sequence, structure, posttranslational modifications, or even identification of a protein based on its m/z value and the m/z values of its digests fragments.

TABLE 1

Protein database available on the internet

| Database | Main Features |
|---|---|
| NCBInr | A non redundant database compiled by the NCBI combining most of the public domain databases (ESTs not included). |

TABLE 1-continued

Protein database available on the internet

| Database | Main Features |
|---|---|
| Swiss Prot | Accurated protein sequence database which strives to provide a high level of annotation, such as the description of the function of a protein, its domain's structure, post-translational modifications, variants, etc. This database offers a minimal level of redundancy and high level of integration with other databases. |
| OWL | A non redundant composite of four publicly available primary sources: SWISSPROT, PIR, (1-3), GenBank (translation) and NRL-3D. SWISSPROT is the highest priority source, all others being compared against it to eliminate identical and trivially different sequences. |
| Genpept | Protein translation of Genbank (ESTs not included). |
| Unknown | A theoretical database used in de novo MS/MS spectral interpretation that is created on-the-fly and contains all amino acid sequence permutations consistent with the parent mass and amino acid composition information contained in an MS/MS spectrum. |

The invention also concerns a method for determining at least one compound expression map in a tissue section, comprising:
1) applying an ionic MALDI matrix on the tissue section,
2) scanning the tissue section with a MALDI mass spectrometer and saving the resulting data, and
3) analyzing the obtained data in the molecular mass window(s) of each distinct compound to create as many maps of compound expression in the tissue section as the number of distinct studied compounds.

Mass spectrometry allows for the analysis of compounds in a wide m/z ratio and the above method can thus be used to determine the expression map in tissue section of a wide range of compounds. In particular, compounds for which the above method can be performed include peptides, nucleic acids, sugars, polymers, lipids, and organic compounds. Organic compounds may include synthetic organic compounds such as drugs, for which a precise localisation in a tissue after administration may be desired.

In a preferred embodiment, the compound for which an expression map is desired is thus selected from peptides, nucleic acids, sugars, polymers, lipids, and organic compounds.

In still a more preferred embodiment, the compound for which an expression map is desired is a peptide or protein, and the invention thus concerns a method for determining at least one protein expression map in a tissue section, comprising:
1) applying an ionic MALDI matrix on the tissue section,
2) scanning the tissue section with a MALDI mass spectrometer and saving the resulting data, and
3) analyzing the obtained data in the molecular mass window(s) of each distinct protein to create as many maps of protein expression in the tissue section as the number of distinct studied proteins.

In a particular embodiment, when lipids are analyzed on a tissue section, the above method for determining at least one lipid, in particular phospholipids, expression map in a tissue section may be modified to comprise:
1) pre-spotting a ionic MALDI matrix onto a MALDI sample carrier,
2) applying said tissue section onto the pre-spotted ionic matrix,
3) scanning the tissue section with a MALDI mass spectrometer and saving the resulting data, and
4) analyzing the obtained data in the molecular mass window(s) of each distinct protein to create as many maps of protein expression in the tissue section as the number of distinct studied proteins.

Such a modified method, in which said ionic matrix is pre-spotted onto the MALDI sample carrier rather than being spotted onto a tissue section deposited on such a MALDI sample carrier, is advantageous for tissue section lipids, in particular phospholipids, analysis. Indeed, lipids, and in particular phospholipids, are compounds that display a significant risk of delocalization when the MALDI matrix is spotted onto the tissue section sample. In contrast, if the ionic MALDI matrix is pre-spotted onto the sample carrier, the risk of delocalization is highly reduced, since the matrix has already crystallized when applying the tissue section sample onto its surface. Such a modified method thus permits to obtain highly precise results for lipids, in particular phospholipids, analysis in tissue sections (see Example 2 and FIG. 14).

According to the invention, a "tissue section" preferably has the following properties: it may be frozen or paraffin-embedded, its thickness is preferably in the order of a mammalian cell diameter, thus comprised between 5 and 20 µm. In the case of a frozen section that was obtained from a frozen tissue using a cryostat, OCT (optimal cutting temperature polymer) is preferably used only to fix the tissue but the frozen tissue is not embedded in OCT, so that tissue sections were not brought into contact with OCT. The tissue section may then be transferred on a MALDI plate composed of any material suitable for further MALDI analysis, including metals, inorganic or organic materials, such as gold, steel, glass fiber, glass, nylon 6/6, silicon, plastic, polyethylene, polypropylene, polyamide, polyvinylidenedifluoride or a glass slice of any thickness coated with conductive metal keeping transparency properties such as nickel or ITO.

By "matrix" is meant any material that, when mixed with the analyte, generates crystalline matrix-embedded analyte molecules that are successfully desorbed by laser irradiation and ionized from the solid phase crystals into the gaseous or vapour phase and accelerated as molecular ions. Commonly used MALDI-MS matrices are generally small, acidic chemicals absorbing at the laser wavelength, including nicotinic acid, cinnamic acid, 2,5-dihydroxybenzoic acid (2,5-DHB), α-cyano-4-hydroxycinnamic acid (CHCA), 3,5-dimethoxy-4-hydroxycinnamic acid (sinapinic acid or SA), 3-methoxy-4-hydroxycinnamic acid (ferulic acid), 3,4-dihydroxycinnamic acid (caffeic acid), 2-(4-hydroxyphenylazo)benzoic acid (HABA), 3-hydroxy picolinic acid (HPA), 2,4,6-trihydroxy acetophenone (THAP) and 2-amino-4-methyl-5-nitropyridine. Protocols for the preparation of these matrices are well-known in the art, and most of these matrices are commercially available. Current commonly used matrices for peptide/protein analysis include α-cyano-4-hydroxycinnamic acid (CHCA), 2,5-dihydroxybenzoic acid (2,5-DHB) and sinapinic acid (SA). DNPH is 2,4-Dinitrophenylhydrazine and is used for aldehydes and ketones detection.

An "ionic matrix" is a complex constituted of a charged matrix and a counter-ion. As MALDI matrices are usually acidic, such ionic matrices are usually prepared by an acid-base reaction between an acid conventional MALDI matrix and an organic base, leading to a proton exchange between the two compounds and resulting in a [Matrix⁻ Base⁺] complex. Despite the usual acidic properties of matrices, some basic matrices also exist, such as the 2-amino-4-methyl-5-nitropyridine (2A4M5NP) matrix. Ionic matrices may thus also be prepared by an acid-base reaction between an acidic and a basic conventional matrix, resulting in a [Acidic matrix⁻/Basic matrix$^{30}$ ] complex after proton exchange. Schematically, the synthesis of an ionic matrix may be performed by mixing equimolar amounts of the two acidic and basic compounds in an organic solvent, such as for instance methanol. After one hour of stirring at room temperature, solvent is evaporated and the resulting ionic matrix is dissolved in an acetonitrile/water solution before use for MALDI analysis.

Precise examples of synthesis of particular matrices are further described in example 2. Any ionic matrix is enclosed in the scope of the present invention. In particular, any acidic conventional matrix may be used as acidic compound for the preparation of a ionic matrix, including nicotinic acid, cinnamic acid, 2,5-dihydroxybenzoic acid (2,5-DHB), α-cyano-4-hydroxycinnamic acid (CHCA), 3,5-dimethoxy-4-hydroxycinnamic acid (sinapinic acid or SA), 3-methoxy-4-hydroxycinnamic acid (ferulic acid), 3,4-di hydroxycinnamic acid (caffeic acid), 2-(4-hydroxyphenylazo)benzoic acid (HABA), 3-hydroxy picolinic acid (HPA), 2,4,6-trihydroxy acetophenone (THAP) and 2-amino-4-methyl-5-nitropyridine. Any organic base or basic conventional matrix may as well be used as basic compound for the preparation of a ionic matrix, including aniline (ANI), N,N-dimethylaniline (DANI), N,N-diethylaniline (DIENI), 1,8-Diazabicyclo [5.4.0]undec-7-ene (DBU), triethylamine ($ET_3NH$), piperidine (PIP), 3-aminoquinoline (3AQ), para nitroaniline, and the 2-amino-4-methyl-5-nitropyridine (2A4M5NP) matrix. Other suitable bases for the preparation of ionic matrices include 3-acétylpyridine (3Apy) and phenylenediamine (PDA).

Particular ionic matrices according to the invention thus include: [CHCA$^-$ANI$^+$], [CHCA$^-$DANI$^+$], [CHCA$^-$DIENI$^+$], [CHCA$^-$DBU$^+$], [CHCA$^-$Et3NH$^+$], [CHCA$^-$PIP$^+$], [CHCA$^-$3AQ$^+$], [CHCA$^-$2A4M5NP$^+$], [SA$^-$ANI$^+$], [SA$^-$DANI$^+$], [SA$^-$DIENI$^+$], [SA$^-$DBU$^+$], [SA$^-$Et3NH$^+$], [SA$^-$PIP$^+$], [SA$^+$3AQ$^+$], [SA$^-$2A4M5NP$^+$], [CHCA$^-$3Apy$^+$] and [CHCA$^-$PDA$^+$]. Particularly advantageous ionic matrices for the implementation of the invention comprise [CHCA$^-$ANI$^+$], [CHCA$^-$DANI$^+$], and [CHCA$^-$2A4M5NP$^+$]. Other particularly advantageous ionic matrices for the implementation of the invention comprise [CHCA$^-$3Apy$^+$] and [CHCA$^-$PDA$^+$].

By a compound or protein expression "map" in a tissue section is meant a two dimensional representation of the expression of said compound or protein in said tissue section. This two dimensional representation is obtained by scanning the tissue section surface with the MALDI analyzer at a defined spot density, performing MALDI analysis on each successive spot and storing both the obtained data and the coordinates of each spot. The higher the spot density, i.e. the smaller the spot area, the more precise is the resulting map. The diameter of a MALDI laser is generally between 50-200 μm depending on the focalisation of the system, so that two adjacent irradiation spots are preferably separated of the laser beam diameter (i.e. 50-200 μm). To allow for the acquisition of precise target molecule map, adjacent spots are preferably separated of at most 300 μm, at most 200 μm, more preferably at most 100 μm, at most 80 μm, at most 60 μm, at most 50 μm, at most 40 μm, most preferably of the diameter of the MALDI laser.

Each spot data is then analyzed in the molecular window of the compound or protein and the signal intensity of the compound or protein is reported at the spot coordinates. Such image reconstruction may be performed automatically using any suitable image reconstruction software known in the art or commercially available. Examples of suitable softwares are the IDL (Interactive Data Language) software, which is commercialized by RSI (RSI Corporate Headquarters. 4990 Pearl East Circle. Boulder, Colo. 80301), flexImaging (Bruker Daltonics, Bremmen, D E), MIT (M. Stoeckli, Novartis, Bâle, Switzerland).

In a preferred embodiment of a method for determining at least one compound, in particular protein, expression map in a tissue section, said ionic MALDI matrix is chosen in the group comprising [CHCA$^-$ANI$^+$], [CHCA$^-$DANI$^+$], [CHCA$^-$DIENI$^+$], [CHCA$^-$DBU$^+$], [CHCA$^-$Et3NH$^+$], [CHCA$^-$PIP$^+$], [CHCA$^-$3AQ$^+$], [CHCA$^-$2A4M5NP$^+$], [SA$^-$ANI$^+$], [SA$^-$DANI$^+$], [SA$^-$DIENI$^+$], [SA$^-$DBU$^+$], [SA$^-$Et3NH$^+$], [SA$^-$PIP$^+$], [SA$^-$3AQ$^+$], and [SA$^-$2A4M5NP$^+$], more preferably in the group comprising [CHCA$^-$ANI$^+$], [CHCA$^-$DANI$^+$], and [CHCA$^-$2A4M5NP$^+$]. Alternatively, said ionic MALDI matrix is selected from [CHCA$^-$3Apy$^+$] and [CHCA$^-$PDA$^+$].

Having generally described this invention, a further understanding of characteristics and advantages of the invention can be obtained by reference to certain specific examples and figures which are provided herein for purposes of illustration only and are not intended to be limiting unless otherwise specified.

EXAMPLE 1

Figure 1:
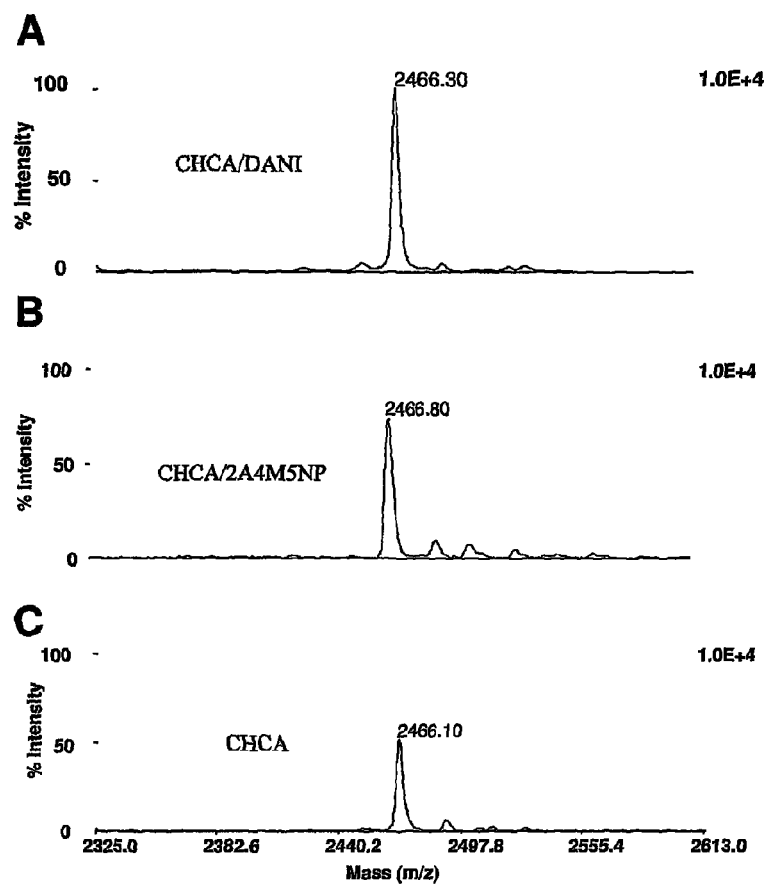
FIG. 1. Typical spectrum of ACTH 18-39 (1 pmol) in linear negative ion mode using A. CHCA/DANI, B. CHCA/2A4M5NP or C. classical CHCA as matrix. In each case, a photography of the matrix was represented near the spectrum considered.

Use of Ionic Matrices for Improved MALDI-MS Peptide/Protein Analysis of Tissue Sections Several ionic matrices were tested for their ability to improve direct peptide/protein analysis in tissue sections.

1.1 Materials and Methods 1.1.1 Materials

α-cyano-4-hydroxycinnamic acid (CHCA), aniline, N,N-dimethylaniline, N,N-diethylaniline, triethylamine, 2-amino-4-methyl-5-nitropyridine (2A4M5NP), 3-aminoquinoline (3AQ), pyridine, 1,8-Diazabicyclo[5.4.0]undec-7ene (DBU), piperidine (PIP), Angiotensin 2, Des-Arg-Bradykinin, Substance P, ACTH 18-39, ACTH 7-38 and Bovine Insulin were obtained from Sigma-Aldrich and used without any further purification. Trifluoroacetic acid (TFA) was purchased from Applied Biosystems. Acetonitrile p.a. and methanol p.a. were from J. T. Baker.

1.1.2 Preparation of Ionic Matrices (IM)

Both ionic matrices used in this study, α-cyano-4-hydroxycinnamic acid/aniline (CHCA/ANI) and α-cyano-4-hydroxycinnamic acid/pyridine (CHCA/PY), were prepared just before the analysis according to the same protocol and as described below. 1 eq. of base (4.8 µL for CHCA/ANI and 4.29 µL for CHCA/PY) were added to a solution of 10 mg/mL of CHCA (1 mL) in acetonitrile/water (2:1, v/v, 0.1% TFA). The mixture was then vortexed and sonicated during 10 minutes before the application on the tissue.

1.1.3 Tissue Preparation

Adult male Wistar rats weighing 250-350 g (animal use accreditation by the French ministry of the agriculture N° 04860) were used in the study and maintained under standard care. Animals were sacrificed by decapitation and immediately dissected to remove the brain. Frozen sections of 15 µm or 20 µm were performed on a cryostat and transferred onto the MALDI plate.

Ovarian med cyst biopsies were obtained from Jeanne de Flandre Hospital of Lille for direct analysis tests.

1.1.4 Sample Solutions

Calibration Mixture

External calibration was performed using a solution of standard neuropeptides and containing 1.6 µM of Bradykinin, 1.6 µM of Substance P, 1.61 µM of ACTH 18-39, 3.2 µM of ACTH 7-38, 4.8 µM Bovine Insulin and 4.8 µM Bovine Ubiquitin in 0.1% TFA/$H_2O$.

Sensivity Tests

Substance P at 2.5 µM in 0.1% TFA/$H_2O$ was diluted 9 times in water in order to get concentrations ranging from 1 pmol/µL to 125 amol/µL.

Intensity Tests

For positive mode analysis, Substance P was used at 0.8 µM. ACTH 18-39 was used at 3.2 µM for negative mode.

1.1.5 Sample Preparation for MALDI/MS Analysis.

Preparation of Matrix Solution for Direct Analysis

Ionic matrix (CHCA/ANI) can be applied directly on the tissue after its conversion in acetonitrile/water (see above). Other ionics matrices were prepared by dissolving 10 mg of compound in 1 mL acetonitrile/water (2:1, v/v, 0.1% TFA).

For classical CHCA, 10 mg of the matrix was dissolved in 1 mL of acetonitrile/water (2:1, v/v, 0.1% TFA/$H_2O$). For SA, 20 mg of matrix was dissolved in the same solvent.

In all cases, a volume of matrix solution was applied onto the frozen cut using a micropipette. The sample was then allowed to dry at room temperature.

Preparation for Classical Analysis

Classical and ionic matrix solutions were prepared according to the same protocol as for direct analysis. In all cases, 1 µL of sample solution and 1 µL of matrix solution were mixed on the MALDI plate according to the procedure of the dried-droplet preparation (Karas, M.; Hillenkamp, F.; *Anal. Chem.* 1998, 60, 2299-2301).

1.1.6 MALDI-MS Analysis

MALDI-TOF mass spectra were performed on a Voyager-DE STR mass spectrometer (Applied Biosystems, Framingham, Mass., USA) with delayed extraction (DE) and operating with a pulsed nitrogen laser at 337µm (3 Hz).

Classical Analysis in Linear Mode

Acquisition parameters were set to: acceleration voltage: 20 kV; $1^{st}$ grid voltage: 94%; guide-wire voltage: 0.05%; extraction delay time: 200 ns.

Direct Analysis in Linear Mode:

Acquisition parameters were: acceleration voltage: 25 kV, $1^{st}$ grid voltage: 94%, guide-wire voltage: 0.05%, extraction delay time: 200 ns.

Direct Analysis in Reflector Mode:

Acceleration voltage: 25 kV, $1^{st}$ grid voltage: 75%, guide-wire voltage: 0.05%, extraction delay time: 200 ns. Each recorded mass spectrum results from the average of 400 laser shots on the area of interest. Slices were visualized in the mass spectrometer with a color CCD camera (SONY).

PSD Mode

Acceleration voltage: 25 kV, $1^{st}$ grid voltage: 72%, extraction delay time: 200 ns. The ion precursors were selected using the timed ion gate (12 mm) of the instrument. Acquisition of the product ions was generally accomplished at 1.0, 0.98, 0.85, 0.75, 0.60, 0.41, 0.27, 0.19, 0.12, 0.067 and 0.05 mirror ratios, and the resulting individual spectra (each an average of 200 shots) were stitched to produce a composite product ion spectrum. In the case of in situ direct analysis, only the three first windows (1.0, 0.98, 0.85) were used.

1.1.7. Direct Analysis of Rat Brain Sections Using a MALDI-TOF-TOF Analyzer with a 50 Hz Laser.

Imaging mass spectra were performed using flexImaging software on a MALDI TOF-TOF UltraFlex II (BRUKER DALTONICS, Bremen, D E) operating with a nitrogen laser emitting at 337 nm (50 Hz) on reflector mode in both positive and negative polarity.

1.2 Results

CHCA/2A4M5NP, CHCA/ANI and CHCA/DANI ionic matrices were first checked on standard compounds, and then used for direct tissue analysis.

1.2.1 Studies with Standards

Evaluation of Spectral Quality in the Positive and Negative Mode.

CHCA/DANI was obtained from the reaction between CHCA and the base N,N-dimethylaniline. On the contrary, CHCA/2A4M5NP was synthesized by acid/base reaction between two classical matrices, CHCA and a basic matrix, 2A4M5NP. Both matrices were evaluated for the production of MS ion signal in the positive and in the negative mode by recording 400 laser shots moving slowly around over the whole spot of a mix of Substance P (500 fmol/µL) or ACTH 18-39 (1 pmol/µL) and the ionic matrix.

Positive Mode

The first step was to compare the energy threshold for ion production of substance P and ACTH 18-39 with respectively CHCA/2A4M5NP, CHCA/DANI and CHCA/ANI matrix. In all cases, variation of fluence was always below to 3% between CHCA and these solid ionic matrices. Furthermore, in all studies of intensity the laser energy was 20% upper the energy threshold for peptide ions which gives a good signal using classical matrices and permits to record a large increase of signal with ionic matrix if necessary.

In the positive mode, significant signal increase was observed using CHCA/2A4M5NP ionic matrix (see following Table 2). The signal was 3.5 fold higher with the ionic matrix in the case of substance P. For Apomyoglobin protein, the signal was also upper of 85% (Table 2) with the ionic matrix than for CHCA, demonstrating the possibility to use this matrix for both peptides and proteins.

ionic matrices in comparison to CHCA (FIG. 1C). Thus, for example, the 2A4M5NP group of the ionic matrix could play a role in the negative mode. The basic properties of this group could help in the ionization step by enhancing proton transfer from the analyte to the matrix. In this respect, deprotonation of the analyte would be more difficult since the matrix only show acid properties. Ionic matrices are salts compounds that could show both characteristics of the acid group and the basic group, as was also observed in organic works.

Taken together, CHCA/DANI and especially CHCA/ANI have shown to be the best matrices in term of signal intensity either in the positive or in the negative mode.

Sensitivity Tests.

To detect compounds in tissues, matrices must be very sensitive due to the low amount of material contained in a slice of 15 µm and particularly when direct analysis is used for the research of biomarkers.

Sensitivity of CHCA/2A4M5NP and CHCA/DANI was tested using substance P and ACTH 18-39 peptides at different concentrations in both positive and negative mode (see following Table 3.

TABLE 2

Analysis of increase of signal in positive and negative mode using CHCA/2A4M5NP or CHCA/DANI vs CHCA.

| matrix | mode | analyte | n[a] | signal[b] intensity range | average[b] intensity | rsd[c] (%) |
|---|---|---|---|---|---|---|
| CHCA/2A4M5NP | + | SP | 10 | 14000-29000 | 21000 | 20 |
| CHCA | + | SP | 10 | 1830-14500 | 5938.5 | 63 |
| CHCA/2A4M5NP | + | ApoMb | 5 | 1851-14500 | 2011 | 7 |
| CHCA | + | ApoMb | 5 | 670-1528 | 1084 | 31.6 |
| CHCA/2A4M5NP | − | ACTH 18-39 | 10 | 2208-8564 | 4380.5 | 50 |
| CHCA | − | ACTH 18-39 | 10 | 1116-7226 | 1982.5 | 65.5 |
| CHCA/DANI | − | ACTH 18-39 | 5 | 5529-18000 | 10218 | 48 |

[a]n are the number of experiments (sample/matrix preparation and analyses) using new matrixes preparation each time.
[b]values of signal intensity range and average are for M + H[+] or M − H[−] and represent the number of counts.
[c]rsd for relative standard deviation Negative Mode Negative mode can be very interesting for direct analysis of tissue especially looking for some special class of compounds like phosphorylated peptides, lipids or phospholipids presenting extensive adduct signals in the positive mode. It can also be used to obtain complementary structural information using PSD. Reduction of salts signals lead to resolution increase and easier interpretation of data.

Generally, negative mode is not so extensively used in MALDI because ion production yields with classical matrices give low rates of negative ions. Here, we have tested the ionic matrices in order to know whether they can present better ion yields in this mode than the conventional matrices. Ionic matrices have been previously tested for low mass compounds (amino acid, see Moghaddam, M. Z.; Heinzle, E.; Tholey, A. *Rapid Commun. Mass Spectrom.* 2004, 18, 141-148), but no studies on peptides/proteins have been yet realised.

In that mode, best signals were recorded using both ionic matrices CHCA/ANI and CHCA/DANI (Table 2, FIG. 1A) and in the same way, good response was obtained for ACTH 18-39 with CHCA/2A4M5NP as matrix (Table 2, FIG. 1B). Minimum signal increase of a factor 2 was observed with

TABLE 3

Sensitivity of 2 new ionic matrices for substance P and ACTH 18-39 (classical preparation) in positive and negative mode.

| matrix | mode | analyte | limit of detection | S/N[a] |
|---|---|---|---|---|
| CHCA/2A4M5NP | + | SP | 100 fmol | 284 |
|  | − | ACTH 18-39 | 150 fmol | 210 |
| CHCA/DANI | + | SP | 250 amol | 87 |
|  | − | ACTH 18-39 | 100 fmol | 1692 |
| CHCA | + | SP | 1 fmol | 70 |
|  | − | ACTH 18-39 | 250 fmol | 340 |

[a]signal to noise ratio.

Best results were obtained using CHCA/DANI. The limit of detection was found to be of 250 amol in the positive mode and 100 fmol in the negative mode. These values have to be compared to CHCA for which the minimum amount detectable is respectively 1 fmol and 250 fmol.

CHCA/2A4M5NP is better in negative mode than CHCA (150 fmol) and presents comparable results in the positive mode.

1.2.2 Direct Analysis in Positive Mode Using Ionics Matrices.

Study of Crystallization on Tissues.

Figure 2:
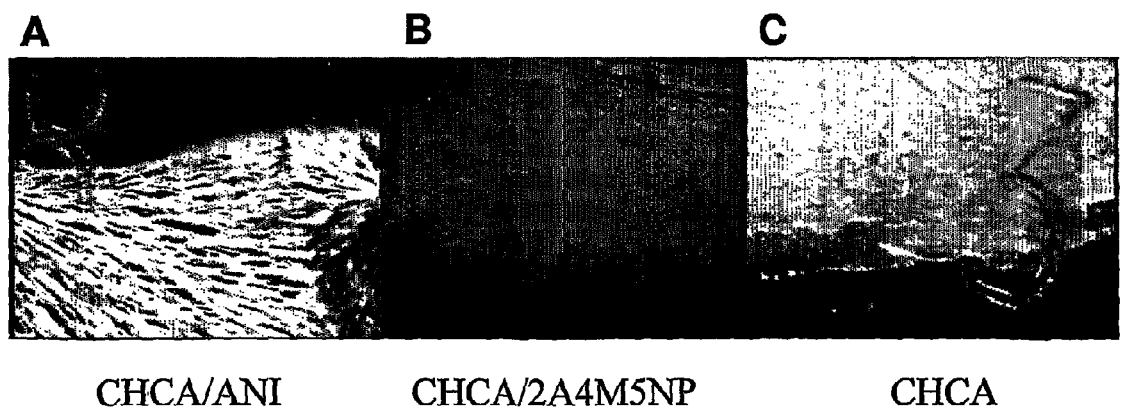
FIG. 2. Crystallization of matrix A. CHCA/ANI, B. CHCA/2A4M5NP or C. classical CHCA on a slice of rat brain after spotting of 20 μL of matrix using micropipette and drying at room temperature.

The crystallization of the three ionic matrices (CHCA/2A4M5NP, CHCA/ANI and CHCA/DANI) on tissue slices was evaluated (see following Table 4 and FIG. 2). To compare crystallization pattern, matrices were simply applied on the whole tissue surface using a micropipette without using sprayer or any other techniques improving crystallization.

TABLE 4

Results in term of cristallisation on the entire slice and in term of intensity of signal in linear and reflector mode considering the positive voltage.

| matrix | form | cristallization on tissue | signals (linear) | signals (reflector) |
|---|---|---|---|---|
| CHCA/ANI | solid | ++++[a] | +++++ | +++++ |
| CHCA/DANI | solid | ++ | +++ | +++ |
| CHCA/2A4M5NP | solid | +++++ | ++ | − |
| CHCA | solid | +++ | +++ | ++ |

[a]"+++++" is the best result and "+" the worst, for "−" no good signal was recorded Two matrices, CHCHA/ANI (FIG. 2A) and CHCA/2A4M5NP (FIG. 2B), have shown to give a very thin crystal layer covering the entire tissue. Very small and homogeneously distributed crystals are observed in the case of CHCA/2A4M5NP (FIG. 2B). For classical matrices, spotting generally gives irregular crystals covering only 50% of the tissue. It must also be noticed that ionic matrices present a high vacuum stability making them very suitable for direct tissue analysis or MALDI imaging since experiments are then longer than for classical MALDI.

For CHCA/DANI, crystallization leads to the formation of big red/orange crystals covering the most part of the tissue. Covering can be improved by increasing the concentration of the matrix (10 mg in 500 μL acetonitrile/0.1% TFA in water 2:1, v/v,), although the size of crystals decreases the homogeneity of the coverage in comparison to classical CHCA.

Direct Analysis in Linear and Reflector Mode Positive Mode)

For comparison of intensity, one spot of an ionic matrix and one spot of CHCA were applied very close together on the same cut. This experiment was repeated more than 5 times on several slices in order to check out reproducibility (see following Table 5).

Figure 3:
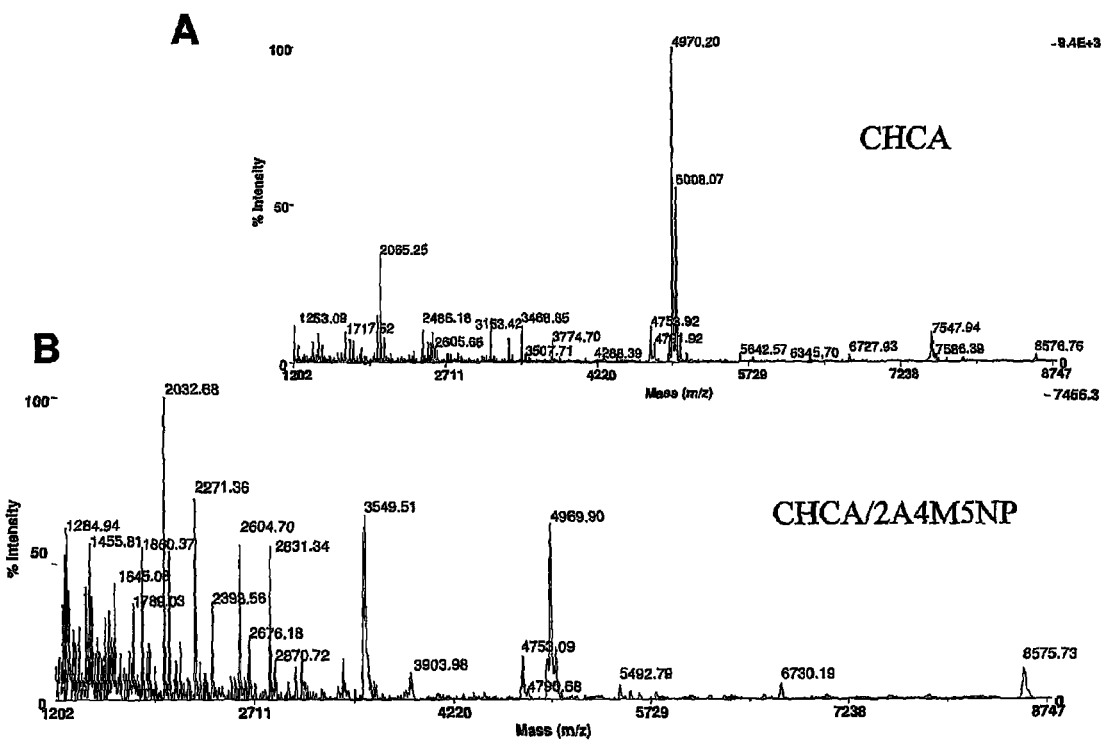
FIG. 3. Typical spectrum obtained in direct analysis using A. CHCA/2A4M5NP and B. CHCA in linear mode (positive polarity).

In linear mode, best signals were obtained using the ionic matrix CHCA/ANI at the same laser energy above the threshold for ion production (Table 5 and FIG. 3). For this matrix, 39 peptides were detected on rat brain sections, 80% of which present a better signal intensity using the ionic matrix than CHCA (Table 5). This increase is especially observed for peptides at m/z 2505.66 and m/z 5072.78. Comparing the number of peptides detected with both matrices, a few ones can only be detected with the ionic matrix (Table 5) and very few only with CHCA. This demonstrates the specificity and reproducibility of ionic matrices for direct proteomic analysis of tissue sections.

TABLE 5

Typical modification of signal using ionic matrix CHCA/ANI in comparison with classical CHCA for linear direct analysis (positive mode) in mass range m/z 1395-8570 for 39 peptides.

| observed m/z | intensity[a] matrix CHCA | intensity[a] matrix ANI | increase factor ANI/CHCA |
|---|---|---|---|
| 1395.8 | 1602.3 | 4181.8 | 2.6 |
| 1789.1 | 490.2 | 2983.4 | 6.1 |
| 1859.1 | 588.4 | 418.8 | 0.7 |
| 1962.2 | 240.5 | 952.8 | 4.0 |
| 2030.0 | 2446.3 | 9500.0 | 3.9 |
| 2070.0 | 1650.7 | 1659.7 | 1.0 |
| 2156.3 | 218.9 | 1216.4 | 5.6 |
| 2377.7 | | 438.7* | |
| 2505.7 | 217.1 | 2250.2 | 10.4 |
| 2602.3 | 458.1 | 1797.5 | 3.9 |
| 2730.7 | 89.0 | 220.2 | 2.5 |
| 2872.4 | 282.9 | 579.3 | 2.0 |
| 3001.4 | | 279.8* | |
| 3027.8 | 172.7 | 303.9 | 1.8 |
| 3381.6 | 329.4 | 643.1 | 2.0 |
| 3534.0 | 284 | 644.7 | 2.3 |
| 3546.7 | 372.1 | 930.8 | 2.5 |
| 4276.9 | | 124.8* | |
| 4285.1 | 96.6 | 856.4 | 8.9 |
| 4304.6 | | 203.3* | |
| 4749.8 | 321.6 | 2268.4 | 7.1 |
| 4787.8 | 552.6 | 667.0 | 1.2 |
| 4939.8 | 1343 | 2632.1 | 2.0 |
| 4966.4 | 6979.2 | 44000.0 | 6.3 |
| 4979.8 | 1452.6 | | |
| 5042.8 | 2889.6 | 2051.6 | 0.7 |
| 5072.8 | 120.5 | 1697.3 | 14.1 |
| 5222.4 | 113.1 | 481.2 | 4.3 |
| 5441.5 | 119.0 | | |
| 5488.3 | | 141.6* | |
| 5638.8 | 342.3 | | |
| 6724.4 | 488.7 | 1082.2 | 2.2 |
| 6761.4 | 181.4 | 191.3 | 1.1 |
| 6803.1 | 305.4 | 141.6 | 0.5 |
| 7066.0 | 186.1 | | |
| 7140.6 | | 208.6* | |
| 7444.8 | | 244.0* | |
| 7541.6 | 182.4 | 410.9 | 2.3 |
| 8570.2 | 718.6 | 2503 | 3.5 |

[a]analysis were performed at the same laser intensity for both cases (considering energy of desorption)
*peptide only detected using ionic matrix For CHCA/DANI, good signals were recorded too, and for peptides with a maximum mass of m/z~1800, CHCA/DANI was better than CHCA. For higher mass, signal was close to that observed with CHCA (data not shown).

For CHCA/2A4M5NP signal intensity is quite good, although the lack of sensitivity of this matrix resulted in the detection of less compounds than with CHCA.

The increase of signal using CHCA/ANI (FIG. 4A) and CHCA/DANI (FIG. 4B) compared to the conventional CHCA matrix (FIG. 4C) was confirmed in the reflector mode. Variation of intensity for different matrices can be easily seen.

Figure 4:
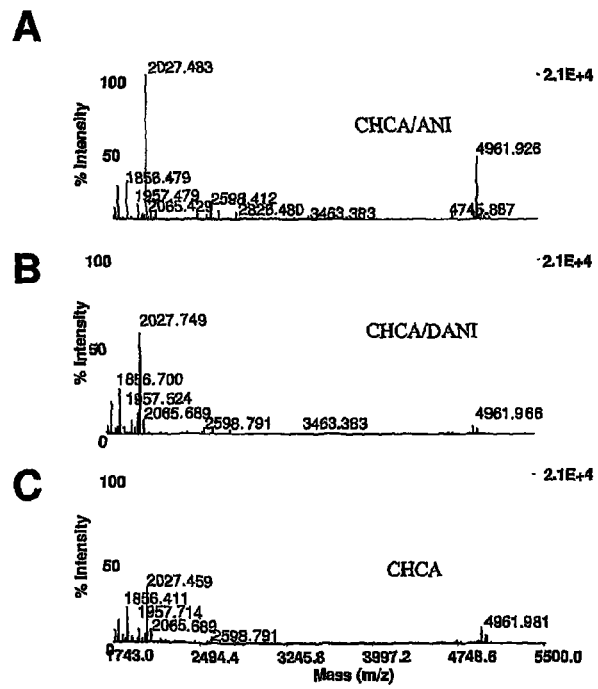
FIG. 4. Minimum increase of signal recorded during direct analysis in reflector mode for matrix A. CHCA/ANI, B. CHCA/DANI and C. classical CHCA, when spots of matrices are very close.
Figure 5:
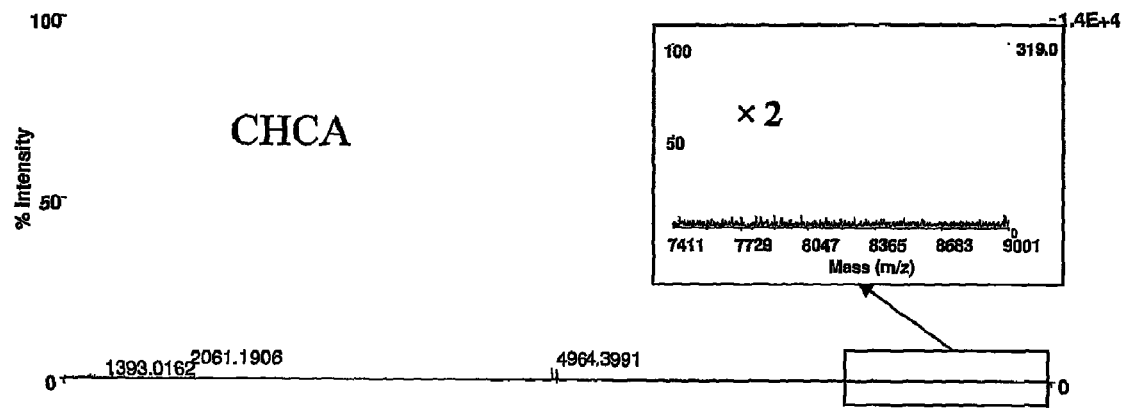
FIG. 5. Spectrum obtained in direct analysis of rat brain in reflector mode, using A. CHCA or B. CHCA/ANI as matrix, for mass range 1000-9000 when spots of matrices are very close.
Figure 5:
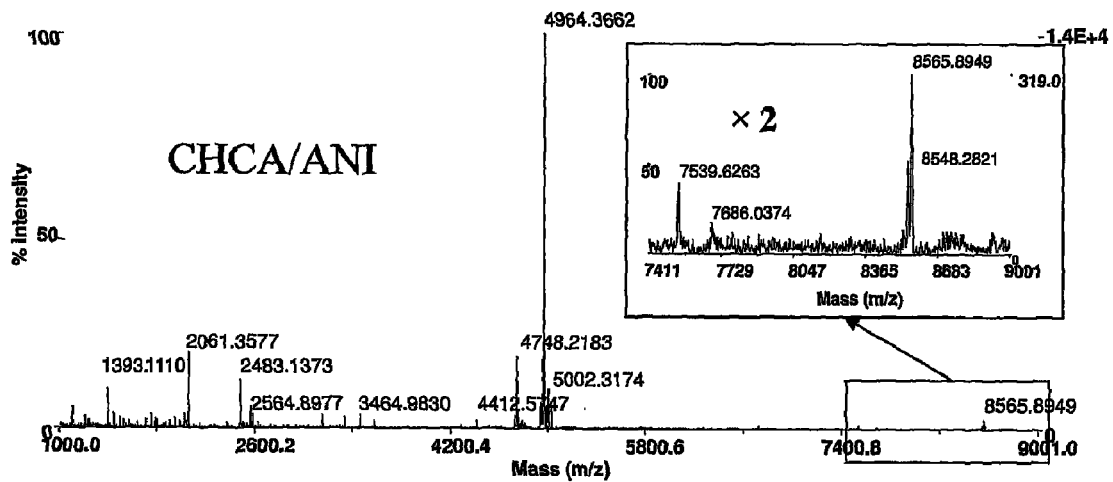

Moreover, in that mode, probably depending on the amount of compounds present in the slice, this increase can be more intense and was observed for a mass range up to m/z 5500 (FIG. 5). Thus, it was possible to detect compounds in the reflector mode directly on the tissue with m/z close to 8600 using matrix CHCA/ANI (FIG. 5B) but not using classical CHCA (FIG. 5A). Experiments were repeated several times to confirm results due to the variability of the intensity and the repartition of molecules in the slice. In all cases a significant increase of intensity was recorded using ionic matrix CHCA/ANI. The same results were also observed using CHCA/DANI, although with a less efficiency than for the aniline derivative (FIG. 4).

Thus, increase of signal observed in classical MALDI analysis using substance P was confirmed in direct analysis on rat brain sections for CHCA/ANI and CHCA/DANI in both linear and reflector modes. Moreover, the signal improvement in reflector mode using these two ionic matrices was the first step to develop fragmentations directly on the tissue using PSD mode.

In Situ Direct PSD with CHCA/ANI

Using this increase of signal, the capacity to produce fragments in PSD mode with ionic matrix CHCA/ANI directly on tissue cuts was explored and compared with the results obtained with classical CHCA, despite the known characteristic of ionic matrix to produce less fragmentation (Li, Y. L.; Gross, M. L. *J Am Soc Mass Spectrom.* 2004, 15, 1833-1837).

Figure 6:
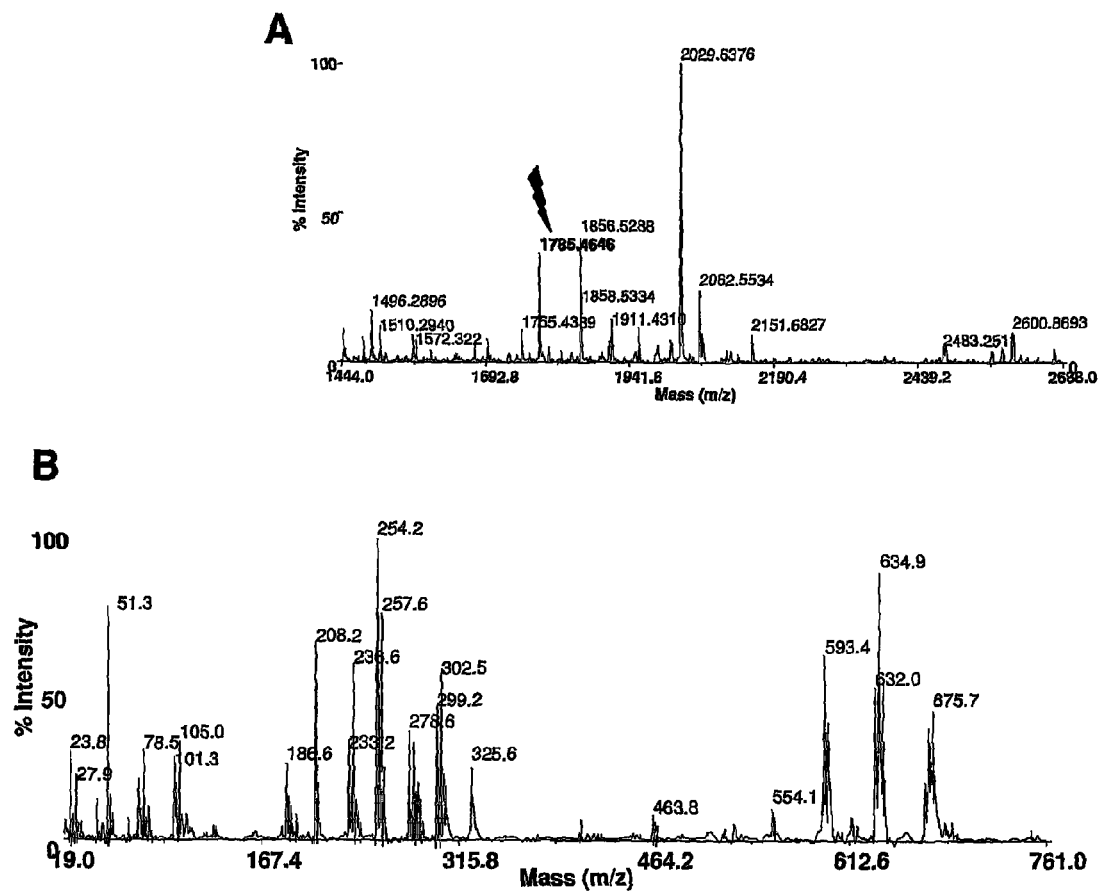
FIG. 6. A. Direct analysis in reflector mode and B. In situ PSD obtained for precursor ion m/z 1785 using ionic matrix CHCA/ANI (collision gaz: Xenon).

Best fragmentation yield recorded in the PSD mode were obtained using CHCA/ANI. For this matrix, partial PSD (FIG. 6B) were obtained directly from the tissue slice for precursor ion 1785 (see FIG. 6A). This in situ PSD was repeated several times on different slices from the same brain, from different brains and for different peptide ion precursors. Repeatable fragments were observed using the same acquisition parameters. Different parameters as extraction delay time, accelerating voltage or laser intensity were studied in order to increase the number of fragments, but no total PSD was obtained. However, partial PSD analysis can be performed for mass up to m/z 2000 (e.g. m/z=1785).

Thus, despite their known characteristic to produce less fragmentation, ionic matrices surprisingly allow, contrary to conventional matrices, for a partial PSD analysis of tissue sections, at least for mass up to m/z 2000.

1.2.3 Direct Analysis in Negative Mode.

Direct analysis in negative mode was also tested, to confirm if the positive results obtained with standards were transposable in direct tissue section analysis. Indeed, the use of negative mode permits to get rid of adducts, which may lead to easier deciphering of the obtained spectra.

Figure 7:
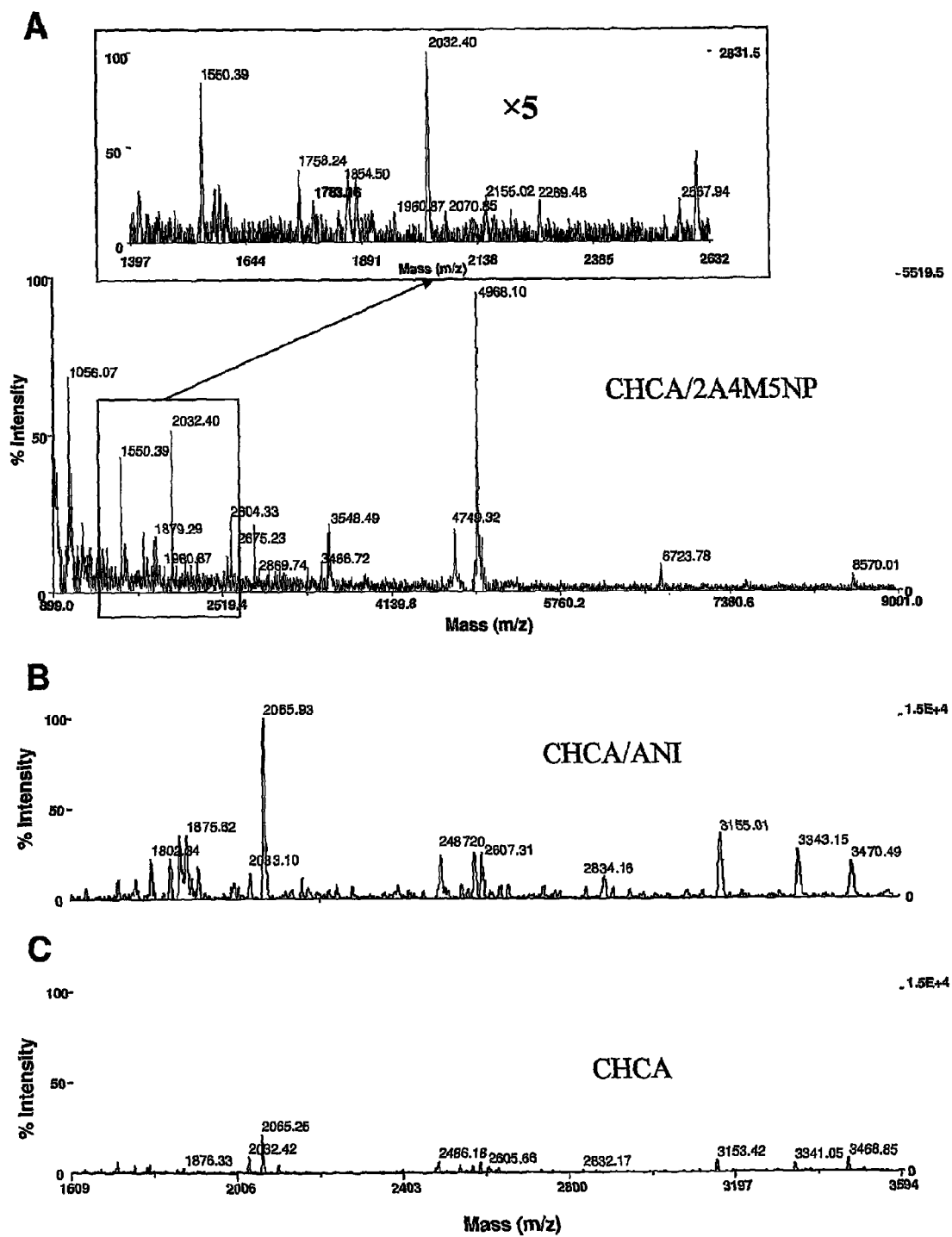
FIG. 7. Direct analysis in linear negative mode using A. ionic matrix CHCA/2A4M5NP for mass range m/z 900-9000, or B. ionic matrix CHCA/ANI or C. classical CHCA for mass range m/z 1609-3595 in case of rat brain.

In negative mode, ionic matrices CHCA2/A4M5NP (FIG. 7A) and CHCA/ANI (FIG. 7B), present interesting ion profiles, showing that this analysis mode may be used for direct analysis of tissue sections using ionic matrices. Great increase of signal intensity was observed with these matrices in comparison to CHCA (FIG. 7C), confirming the results obtained with standards. As previously shown, CHCA/DANI and especially CHCA/ANI (FIG. 7B) were again the matrices leading to higher increase of intensity and presenting the best sensitivity.

Figure 8:
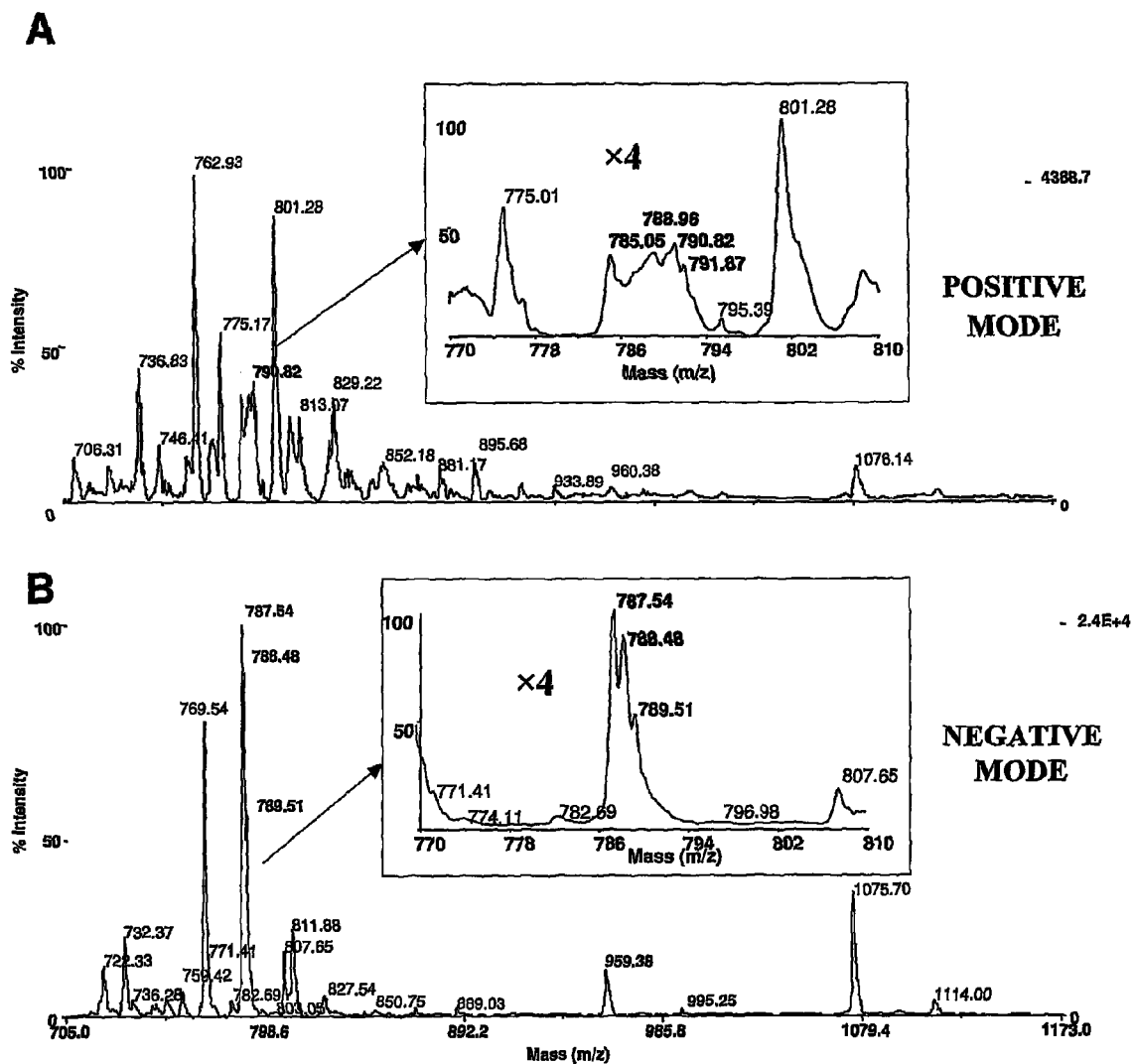
FIG. 8. Typical direct analysis A. in linear positive mode and B. in linear negative mode at the same localisation using CHCA/DANI in case of rat brain. (mass range: 700-1170).

We also compared direct analysis in negative and positive modes. For this, one spot with CHCA/DANI was performed and spectra in both positive (FIG. 8A) and negative mode (FIG. 8B) were recorded on this same only by switching high voltages. Due to the lower sensitivity of the negative mode, less signal were observed in this mode. Nevertheless, some compounds can be detected with a higher intensity (e.g. m/z 959 or m/z 995 (FIG. 8B)). Moreover, adducts suppression give easier readability of the mass spectra. For the mass range below to m/z~1200, resolution is greatly improved as observed for signals at m/z=787 or 811 (FIGS. 8A and 8B) due to probably adducts of lipids detected in positive mode.

Thus, ionic matrices such as CHCA/DANI, CHCA2/A4M5NP and CHCA/ANI allow, thanks to a high increase in signal intensity, for the use of linear negative mode analysis, thus enabling to obtain more readability of the obtained spectra.

1.2.4 Application to Ovarian Normal and Cancerous Tissue Biopsies

The research of potential biomarkers is usually based on differential display analysis of patient presenting a specific pathology compared to healthy patient. In the case of cancer, many publications describe differential analysis by mass spectrometry using Surface Enhanced Laser Desorption Ionization (SELDI) applied to biological fluids but especially to serum. Classically, many proteomic studies imply the comparison of 2D electrophoresis map before the identification of potentially interesting spots by mass spectrometry.

Figure 9:
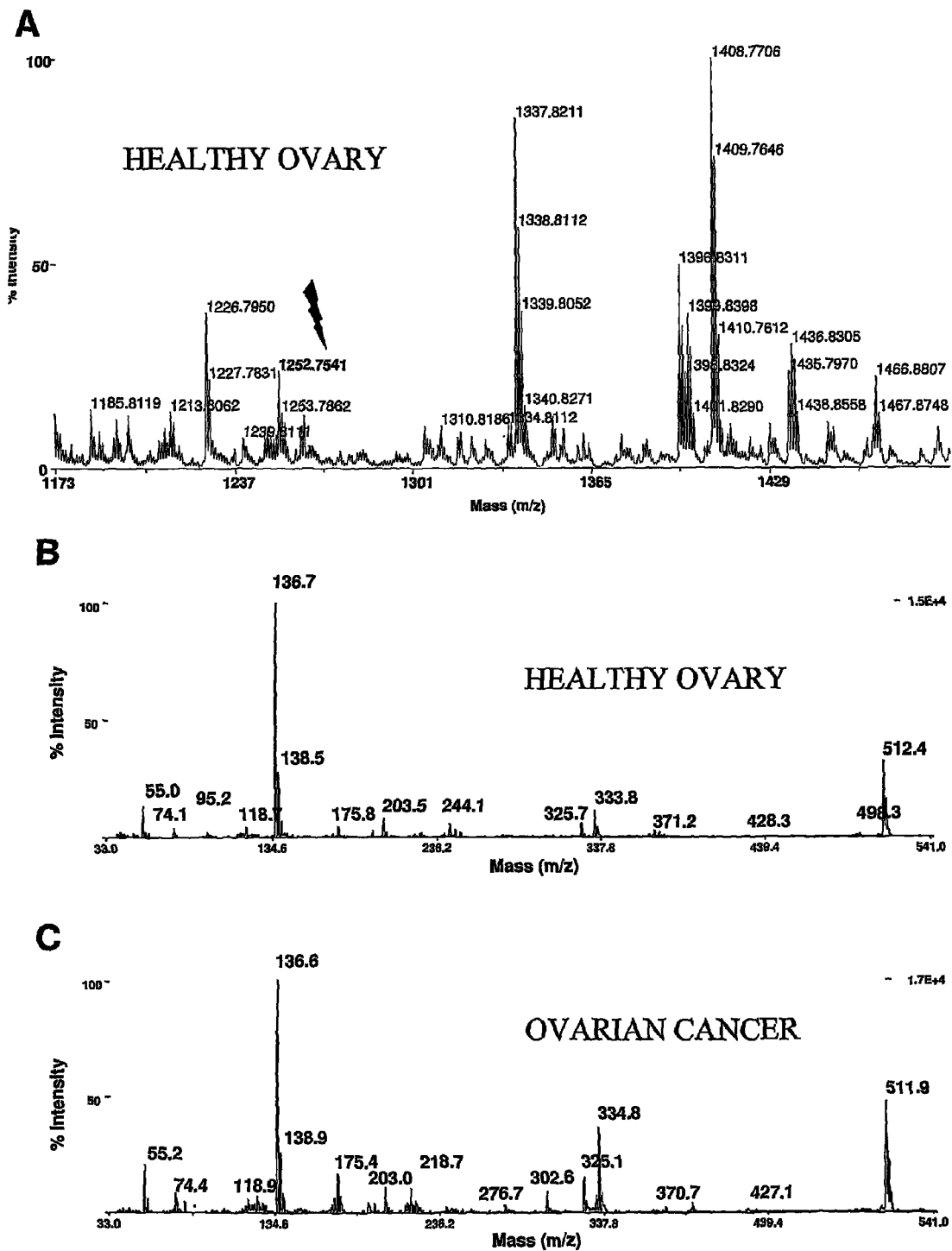
FIG. 9. A. Direct analysis of healthy ovary tissue using matrix CHCA/ANI in positive reflector mode for mass range m/z 1173-1493, and In situ PSD performed on two different slices in case of B. healthy ovary for parent m/z 1252.36 and C. ovarian cancer for parent ion m/z 1252.24 using ionic matrix CHCA/ANI with the three first acquisition windows (mirror ratios 1.0, 0.98 and 0.85).

An alternative method is to use direct tissue analysis by MALDI and to compare protein profiles recorded from healthy tissue to cancerous ones. Cancer markers are very difficult to find out in the body fluids. On the contrary, direct analysis of cancerous tissues would allow for selection of high confidence potentially interesting markers. The potentiality of direct analysis of healthy and cancerous ovarian tissue sections using ionic matrices was thus explored. The analysis of two tissue pieces coming from biopsy of a healthy patient and a patient with ovarian cancer generates very rich ion profiles (FIG. 9A). Particularly high intensity signal was observed for CHCA/ANI as matrix.

First comparison of these very rich ion profiles could lead to some ambiguities with ions having close masses but not isobaric despite careful calibration of the mass spectra. For example, a peptide presenting a peak at m/z1252.75 in the healthy ovary (FIG. 9A) and 1252.4 in the cancerous tissue was observed.

In order to check out whether these two different peptides are identical due to different tissue thickness leading to decalibration, PSD analysis was performed on these peaks. As previously described, only partial PSD were possible. But even though, the same fragment ions were present on the PSD spectra confirming that the same molecule is present in both the healthy patient tissue (FIG. 9B) and the ovarian cancer tissue (FIG. 9C) at this m/z value. These results clearly show the surprising and significant interest of using ionic matrices for direct analysis of tissue section by MALDI-MS, since despite their known characteristic to produce less fragmentation, ionic matrices allow, contrary to conventional matrices, to resort to partial in situ PSD analysis, thus enabling to clear up ambiguities that may arise in the very rich ion profiles generated by direct analysis of tissue sections.

Figure 10:
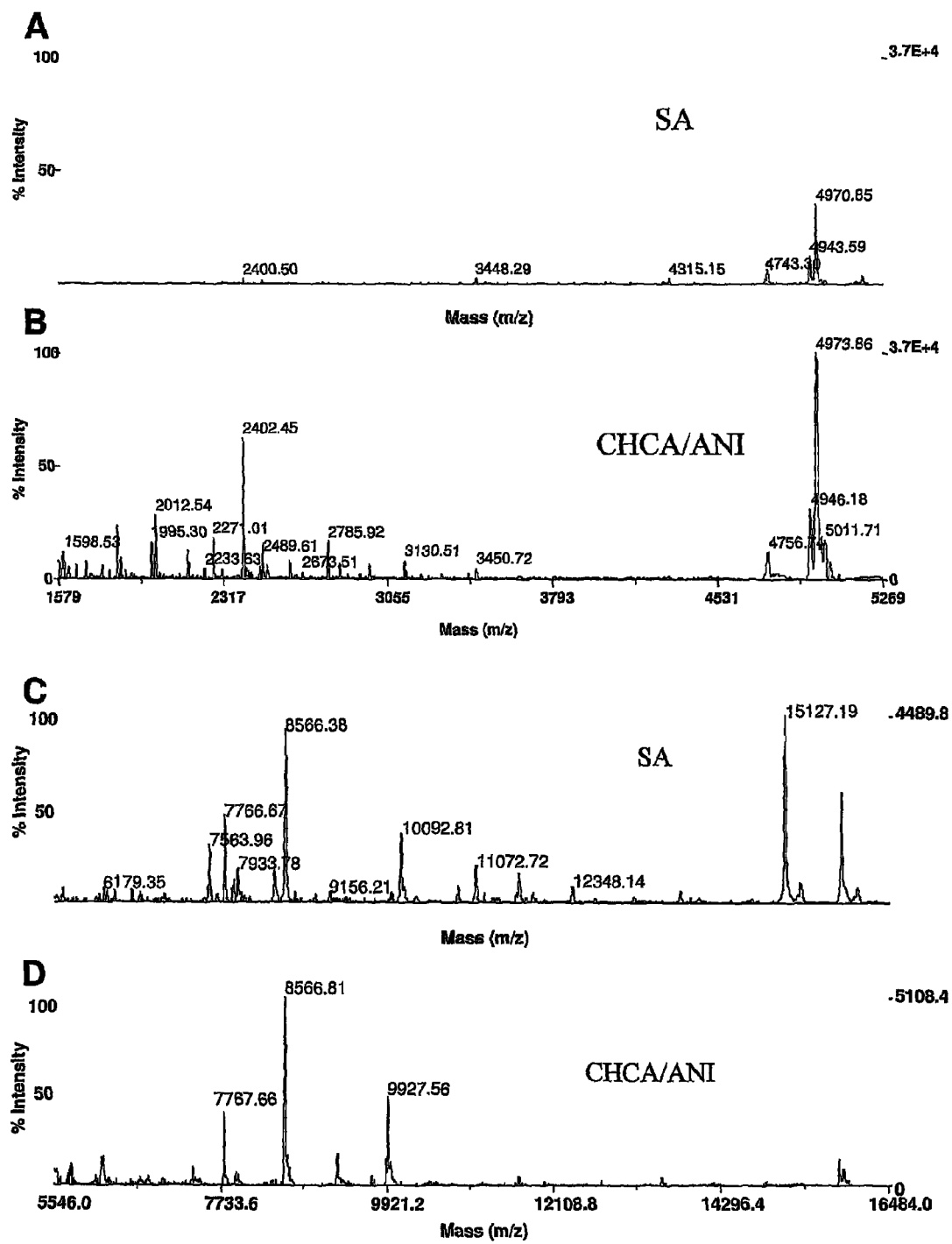
FIG. 10. Direct analysis of healthy ovary tissues using SA (A. and C.) and using ionic matrix CHCA/ANI (B. and D.) in linear positive mode, for mass range mass m/z 1580-5270 (A. and B.) and m/z 5546-16484 (C. and D.). Laser fluence was optimised in order to have maximum of compounds detected for the mass range considered.

On the ovarian biopsies, mass spectra recorded with Sinapinic acid (SA) and those obtained with CHCA/ANI ionic matrix were also compared. Sinapinic acid was used here because this matrix has been shown to be the most employed one for direct tissue analysis (Schwartz, S. A.; Reyzer, M. L.; Caprioli, R. M. *J. Mass Spectrom.* 2003, 38, 699-708). As expected, much better signals were detected using the ionic matrix for mass range below m/z 5000 (FIGS. 10A and 10B) and results with comparable sensitivity were observed up to m/z 10000 (FIGS. 10C and 10D), although over m/z 10000 traditional Sinapinic Acid gave better results (FIGS. 10C and 10D). Anyway, these results clearly show that for m/z inferior to 10000, CHCA/ANI ionic matrix allows for a much more sensitive and precise direct analysis of peptides/proteins in tissue sections, compared to the usually used Sinapinic acid (SA) matrix.

1.2.5 Direct Analysis of Rat Brain Tissue Sections Using a MALDI-TOF-TOF Analyzer with a 50 Hz Laser.

Usually, for direct analysis of peptides/proteins in tissue sections, only a 2 or 3 Hz MALDI laser is used. Indeed, conventional MALDI matrices such as SA, or CHCA are not suitable for analysis with a higher frequency laser, because of the abundant material ejected during desorption process.

In contrast, ionic matrices present smaller volumes of material ejected and direct analysis of rat brain tissue sections was successively carried out with CHCA/ANI using a MALDI-TOF-TOF analyzer with a 50 Hz laser in negative and positive mode using the same cut.

Figure 11:
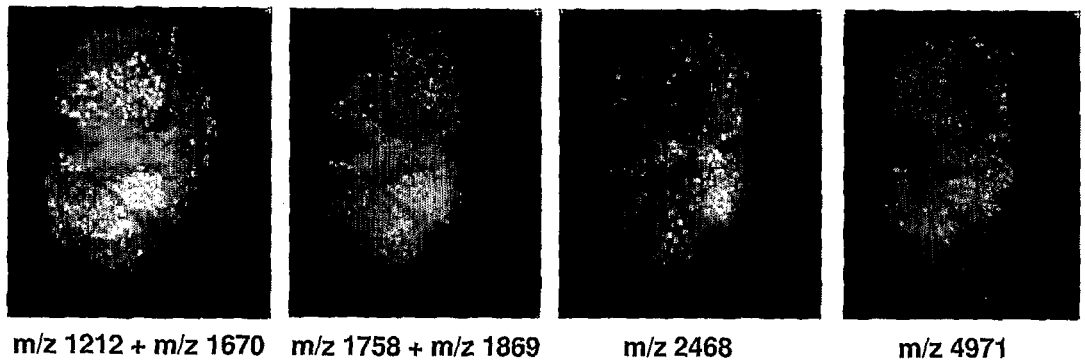
FIG. 11. Direct analysis of peptides/proteins in rat brain tissue sections. Here are shown the reconstructed images of the expression maps of several compounds with distinct m/z ratios in positive or negative polarity using a 50 Hz MALDI-TOF-TOF analyzer in the reflector mode.
Figure 11:
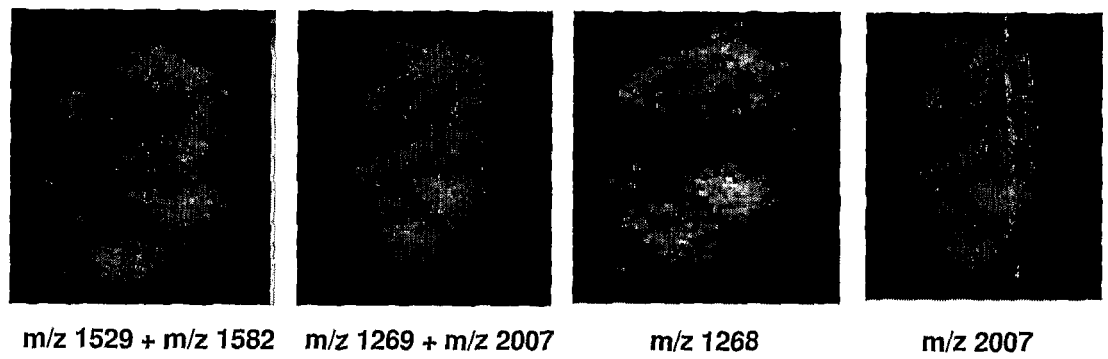

Results are displayed both in the positive and the negative mode in FIG. 11 and demonstrate that ionic matrices, contrary to conventional matrices, allow the use of higher frequency laser as in MALDI-TOF-TOF which is a crucial result.

Indeed, such powerful MALDI-TOF-TOF analyzers allow for a much more rapid and much more detailed structural analysis of peptides and proteins, directly in tissue sections.

In particular, the possibility to use powerful MALDI-TOF-TOF analyzers allows for direct in situ peptide sequencing (MS/MS) of higher molecular weight than what is possible using PSD analysis.

In addition, images were obtained by scanning a whole rat brain section in 10 000 positions, averaging 100 shots per position in reflector mode for several distinct m/z ratios using a MALDI LIFT/TOF (50 Hz laser repetition rate), either with ionic matrix CHCA/ANI or with conventional matrix CHCA in positive or negative mode. More precisely, a first scan was acquired in positive mode, the section was rescanned on the same positions in negative mode. Finally, a last scan was performed in the positive mode again.

Figure 12:
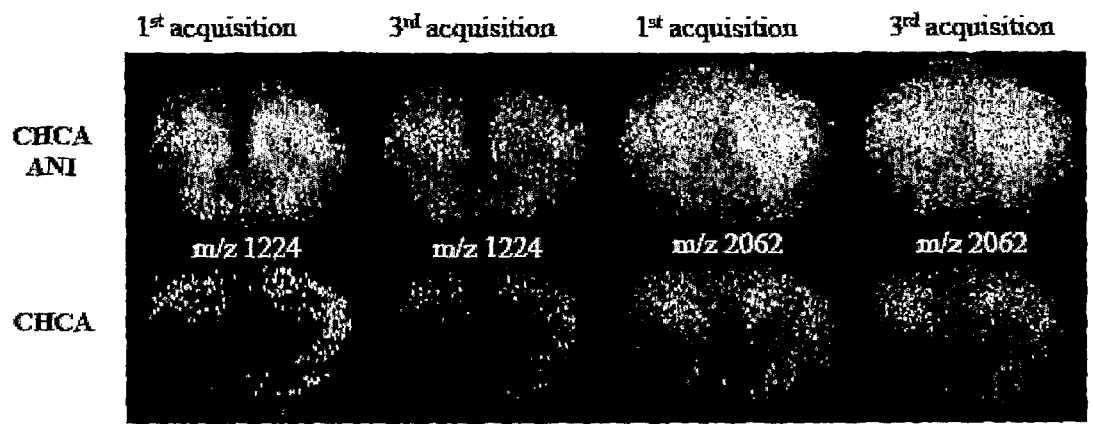
FIG. 12. MALDI-IMS using MALDI LIFT/TOF in reflector mode (50 Hz laser repetition rate, 10 000 positions scanned), with ionic matrix CHCA/ANI and with CHCA in positive mode for the first and the third acquisition on the same rat brain slice. Images have been reconstructed using FlexImaging software and represent the repartition of a m/z in the tissue slice. Same imaging parameters were used for all acquisitions.

Results show that using CHCA/ANI ionic matrix, no major decrease in signal intensity was noticed between the first and the third scan (see FIG. 12). For CHCA, a decrease of intensity was clearly observed as illustrated in FIG. 12 for m/z 1224. After three scans the section was still totally covered with ionic matrix which was not the case with classical CHCA. This inevitably leads to loss in image resolutions, since some peaks are no more observed in the corresponding mass spectra (e.g. m/z 2062 and m/z 1224).

Figure 13:
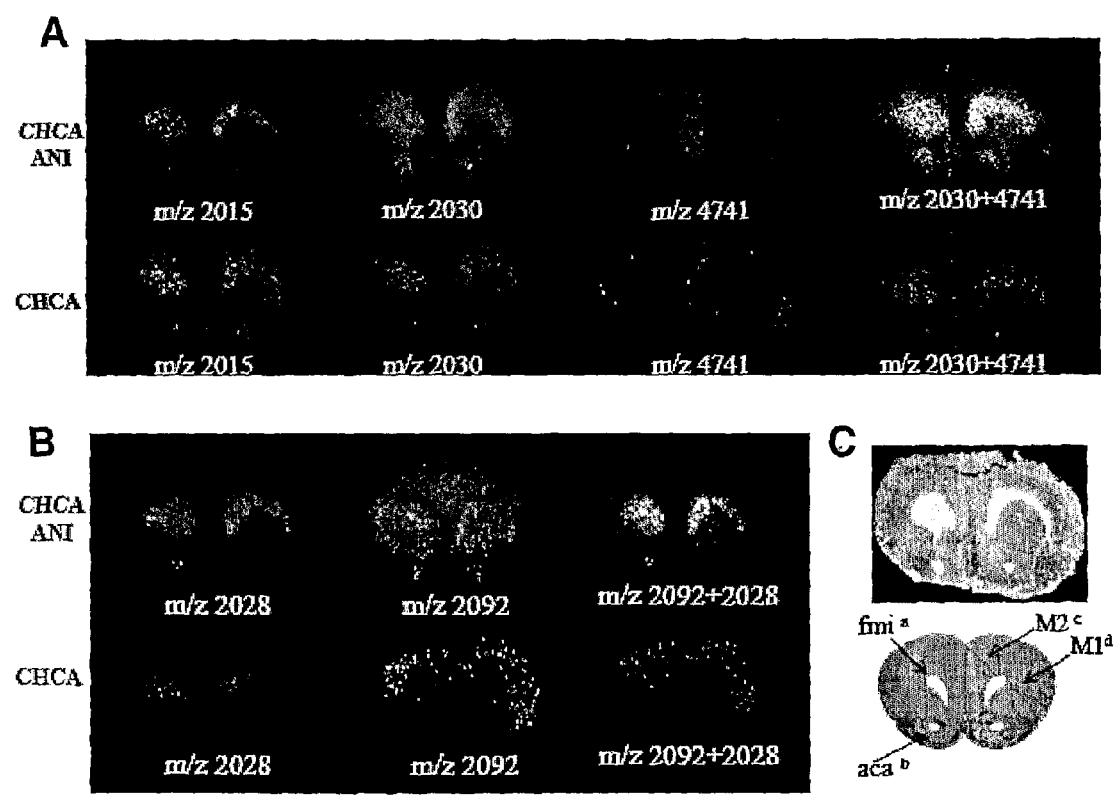
FIG. 13. MALDI-IMS using MALDI LIFT/TOF in reflector mode at 50 Hz repetition rate with ionic matrix CHCA/ANI and CHCA in positive (A) and negative mode (B). MALDI Imaging can be compared with rat brain anatomy (C). For CHCA/ANI and CHCA, acquisitions in both polarities were performed on the same rat brain cut. Images have been reconstructed with the same parameters for ionic matrix and CHCA using FlexImaging software and represent the repartition of a m/z in the tissue slice. Images with two colours correspond to the superposition of two m/z images. ([a] forceps minor of corpus callosum [b] anterior commissure and [c,d] mortor cortex)
Figure 14:
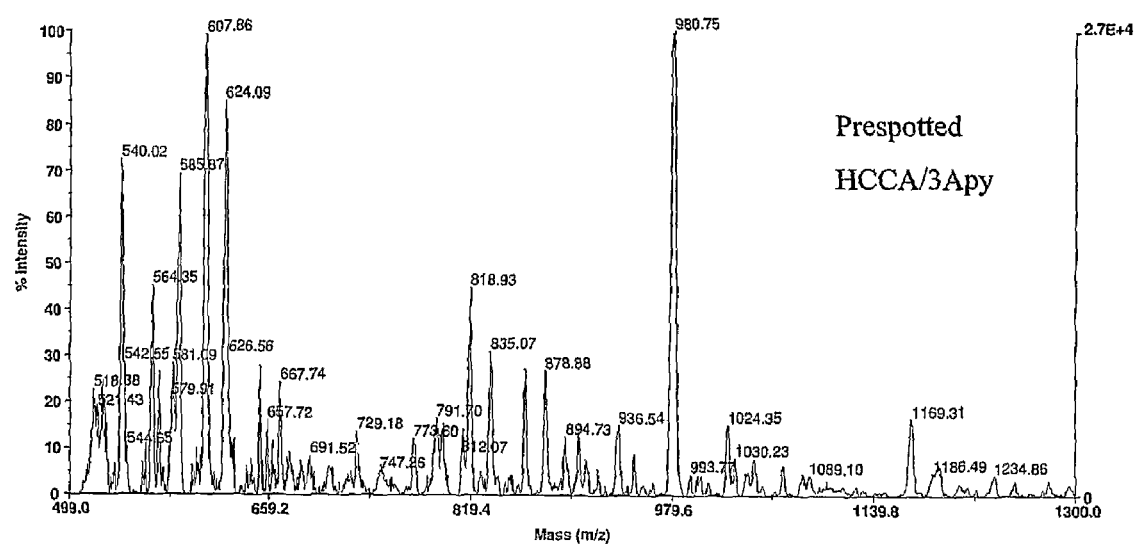
FIG. 14. Direct analysis of phospholipids in a rat brain tissue section using a pre-spotted [CHCA⁻3Apy⁺] ionic matrix.

Several images reconstructed from both positive and negative data for some m/z ratio are shown in FIG. 13A and FIG. 13B. The images demonstrate a fewer delocalization for CHCA/ANI ionic matrix than for CHCA conventional matrix considering a classical deposition using a micropipette. This phenomenon is well illustrated by the molecular image reconstructed for peptide at m/z 2015 (FIG. 13A). This was attributed to the very fast and homogenous crystallization of this matrix on the tissue. The comparison of the images using CHCA conventional matrix and CHCA/ANI ionic matrix shows a better resolution for CHCA/ANI with a higher signal intensity and detection. Rat brain regions can be easily recognized by comparing MALDI ionic matrix imaging to rat brain maps (FIG. 13C). For instance, in positive mode, peptide at m/z 2015 are found to be in forceps minor of corpus callosum (fmi) and anterior commissure (aca), but peptide at m/z 4741 is in the rest of brain. For m/z 2028 in negative mode and m/z 2030 in positive mode, similar localization was observed despite of worse detection in negative mode for other regions than corpus callosum.

Better sensitivity using CHCA/ANI ionic matrix was confirmed for several ions as for m/z 4741 (positive mode) or m/z 2092 (negative mode). Consequently, precise localization of these peptides using MALDI imaging is impossible using CHCA conventional matrix when it can be done using CHCA/ANI ionic matrix.

1.3 Conclusion

The results described here clearly highlight the benefits of using ionic matrices for direct analysis of tissue sections by MALDI-MS, compared to conventional matrices such as CHCA or SA. Indeed, a global enhanced sensitivity was observed, with much increased signals, in all MALDI-MS analysis modes (linear, reflector, positive and negative) as seen for MALDI imaging application.

In addition, this increase in signals allows for the use of negative mode, which leads to a new type of MALDI imaging due to the detection of new compounds and readability of the obtained spectra, which is of particular interest for the direct analysis of tissue sections, since this kind of sample generates particularly rich ion profiles, compared to purified, extracted samples.

Moreover, the use of ionic matrices surprisingly allows for the generation of partial PSD analysis data, thus enabling to obtain structural data, which further permits to clear up ambiguities in the spectra. Such ambiguities are usually linked to the difficulties to directly analyze tissue sections with variable parameters such as the tissue section thickness, which may lead to decalibration.

Finally and importantly, contrary to conventional matrices, ionic matrices allow for the use of MALDI-TOF-TOF analyzers with high frequency lasers (at least 50 Hz), which permits to generate much more detailed structural information and on higher molecular weight components that PSD or MS/MS analysis. It also permits at least a three times sequential analysis of the same tissue section with no signal decrease, which is not possible using a conventional matrix.

Thus, thanks to the use of ionic matrices, much more rapid, sensitive and precise data may be obtained in the direct peptide/protein analysis of tissue sections, compared to conventional matrices.

EXAMPLE 2

Use of Pre-Spotted Ionic Matrices for Improved MALDI-MS Phospholipids Analysis of Tissue Sections

2.1 Methods

Preparation of Ionic Matrices (IM). all Ionic Matrices as CHCA/DAP or CHCA/3apy can be produced using classical protocols used for ionic liquids synthesis. 50 mg of CHCA or other MALDI matrix are dissolved in 20 mL of methanol. An equimolar amount of base was added. The solution was mixed for one hour, and the solvent evaporated in a vacuum evaporator for 45 minutes (T=50° C., P=40 mbar). The resulting compound was placed in a dessicator for 30 minutes to eliminate residual solvent and stored at −20° C. Just before use, the ionic matrices were prepared by dissolving 10 mg of compound in 1 mL acetonitrile/water (2:1, v/v, 0.1% TFA).

Ionic matrices used in this study, can also be prepared just before use, following a faster protocol: 1 equivalent of base (5.8 µL for CHCA/3Apy) was added to a solution of 10 mg/mL of CHCA (1 mL) in acetonitrile/water (2:1, v/v, 0.01% TFA). The mixture was then vortexed and sonicated for 10 minutes before use.

For pre-spotted ionic matrix, ionic matrix was spotted onto the MALDI plate or onto a conductive support then keep drying at room temperature. After crystallization of the ionic matrix, the tissue was applied onto the dry matrix then introduced into the mass spectrometer for analysis.

2.2 Results

As displayed on FIG. 12, prespotted [CHCA$^-$3Apy$^+$] ionic matrix permits a sensitive and good quality analysis of phospholipids in a rat brain tissue section, while significantly limiting risks of delocalization of such molecules.

The invention claimed is:

1. A method for studying protein expression in a tissue section, comprising:
   1) applying an ionic MALDI matrix onto the tissue section, wherein said ionic matrix is solid at room temperature and selected from the group consisting of [CHCA⁻ANI⁺], [CHCA⁻DANI⁺], [CHCA⁻2A4M5NP⁺], [CHCA⁻3APY⁺], [CHCA⁻PDA⁺], [SA⁻ANI⁺], [SA⁻DANI⁺], [SA⁻DIENI⁺], [SA⁻Et3NH⁺], [SA⁻PIP⁺], [SA⁻3AQ⁺], and [SA⁻3APY⁺];
   2) scanning the tissue section with a MALDI mass spectrometer and saving the resulting data, and
   3) in each analyzed point, determining the protein composition by comparing the obtained spectrum with database proteins molecular weights and spectra.

2. A method for determining at least one-peptide or protein expression map in a tissue section, comprising:
   1) applying an ionic MALDI matrix on the tissue section, wherein said ionic matrix is solid at room temperature and selected from the group consisting of [CHCA⁻ANI⁺], [CHCA⁻DANI⁺], [CHCA⁻2A4M5NP⁺], [CHCA⁻3APY⁺], [CHCA⁻PDA⁺], [SA⁻ANI⁺], [SA⁻DANI⁺], [SA⁻DIENI⁺], [SA⁻Et3NH⁺], [SA⁻PIP⁺], [SA⁻3AQ⁺], and [SA⁻3APY⁺];
   2) scanning the tissue section with an MALDI mass spectrometer and saving the resulting data, and
   3) analyzing the obtained data in the molecular mass window(s) of each distinct peptide or protein to create as many maps of peptide or protein expression in the tissue section as the number of distinct studied peptide(s) or protein(s).

3. The method of claim 1, wherein said ionic MALDI matrix is selected from the group consisting of [CHCA⁻ANI⁺], [CHCA⁻DANI⁺], and [CHCA⁻2A4M5NP⁺].

4. The method of claim 1, wherein said ionic MALDI matrix is selected from the group consisting of [CHCA⁻3Apy⁺] and [CHCA⁻PDA⁺].

5. The method of claim 2, wherein said ionic MALDI matrix is selected from the group consisting of [CHCA⁻ANI⁺], [CHCA⁻DANI⁺], and [CHCA⁻2A4M5NP⁺].

6. The method of claim 2, wherein said ionic MALDI matrix is selected from [CHCA⁻3Apy⁺] and [CHCA⁻PDA⁺].

7. An ionic matrix that is solid at room temperature and selected from the group consisting of [CHCA⁻DANI⁺], [CHCA⁻2A4M5NP⁺], [SA⁻ANI⁺], [SA⁻DANI⁺], [SA⁻PIP⁺], [SA⁻3AQ⁺], [SA⁻2A4M5NP⁺], [CHCA⁻3Apy⁺], [CHCA⁺PDA⁺], and [SA⁻3APY⁺].

8. The method of claim 1, wherein said ionic MALDI matrix is selected from the group consisting of [CHCA⁻DANI⁺], [CHCA⁻2A4M5NP⁺], [CHCA⁻3APY⁺], [CHCA⁻PDA⁺], [SA⁻ANI⁺], [SA⁻DANI⁺], [SA⁻PIP⁺], [SA⁻3AQ⁺], and [SA⁻3APY⁺].

9. The method of claim 2, wherein said ionic MALDI matrix is selected from the group consisting of [CHCA⁻DANI⁺], [CHCA⁻2A4M5NP⁺], [CHCA⁻3APY⁺], [CHCA⁻PDA⁺], [SA⁻ANI⁺], [SA⁻DANI⁺], [SA⁻PIP⁺], [SA⁻3AQ⁺], and [SA⁻3APY⁺].

10. The method of claim 3, wherein said ionic MALDI matrix is selected from the group consisting of [CHCA⁻DANI⁺], and [CHCA⁻2A4M5NP⁺].

11. The method of claim 5, wherein said ionic MALDI matrix is selected from the group consisting of [CHCA⁻DANI⁺], and [CHCA⁻2A4M5NP⁺].

* * * * *